United States Patent [19]

Visveshwara et al.

[11] Patent Number: 4,915,103
[45] Date of Patent: Apr. 10, 1990

[54] VENTILATION SYNCHRONIZER

[75] Inventors: Nadarasa Visveshwara; Bruce J. Freeman, both of Fresno, Calif.

[73] Assignee: N. Visveshwara, M.D., Inc., Fresno, Calif.

[21] Appl. No.: 137,517

[22] Filed: Dec. 23, 1987

[51] Int. Cl.$^4$ .............................................. A62B 7/00
[52] U.S. Cl. ........................... 128/204.23; 128/204.21
[58] Field of Search ............. 128/204.23, 723, 204.26, 128/204.21, 204.18

[56] References Cited

U.S. PATENT DOCUMENTS

| | | | |
|---|---|---|---|
| 3,400,712 | 9/1968 | Finan | 128/204.23 |
| 3,572,317 | 3/1971 | Wade | 128/723 |
| 3,923,055 | 12/1975 | Hammacher | |
| 3,946,729 | 3/1976 | Hanna | 128/204.23 |
| 3,951,143 | 4/1976 | Kitrilakis et al. | |
| 4,141,356 | 2/1979 | Smargiassi | 128/204.23 |
| 4,211,221 | 7/1980 | Schwanbom et al. | 128/204.26 |
| 4,357,936 | 11/1982 | Ellestad et al. | 128/204.23 |
| 4,401,115 | 8/1983 | Monnier | 128/204.23 |
| 4,450,838 | 5/1984 | Miodownik | 128/204.23 |
| 4,686,974 | 8/1987 | Sato et al. | 128/204.23 |
| 4,686,975 | 8/1987 | Naimon et al. | 128/204.23 |
| 4,744,356 | 5/1988 | Greenwood | 128/204.26 |

FOREIGN PATENT DOCUMENTS

| | | | |
|---|---|---|---|
| 973253 | 8/1975 | Canada | 128/723 |
| 1210849 | 2/1986 | U.S.S.R. | 128/204.23 |

OTHER PUBLICATIONS

"Observations with an Electrical Impedance Respirometer", by McCally et al., The American Journal of Medical Electronics, Oct.-Dec. 1963, pp. 322-327.

Primary Examiner—Edgar S. Burr
Assistant Examiner—Aaron J. Lewis
Attorney, Agent, or Firm—Majestic, Parsons, Siebert & Hsue

[57] ABSTRACT

The electrical impedance between two selected points on a person's chest will change in response to spontaneous respiration. The rising edge of the impedance signal is detected to indicate the onset of spontaneous inspiration. The supply of gas by the respirator is synchronized with a selected point during the spontaneous inspiration time period. Apnea conditions are detected to trigger a backup system for supplying gas to the patient periodically despite the lack of spontaneous respiration. If so desired, the triggering and turning off of the respirator need not be synchronized to be simultaneous with the onset of inspiration and exhalation; instead, these may be accomplished at selected times after the initiation of inspiration or exhalation. The triggering and turning off of the respirator can also be accomplished in a manner so that the effects of a wandering baseline are minimized. Instead of using the electrical impedance between two points on a person's chest to indicate spontaneous respiration, other signals may also be used which may for example be electromyograms, signals indicating chest muscle contractions, pneumatic device signals indicating the movement of patient's abdomen and ultrasound signals indicating the movement of the patient's diaphragm.

6 Claims, 8 Drawing Sheets

VENTILATION SYNCHRONIZER

BACKGROUND OF THE INVENTION

This invention relates to systems for synchronizing the supply of gas by a respirator with spontaneous respiration. More specifically, this invention relates to a method and apparatus for controlling a respirator in order to synchronize the supply of gas by the respirator with the respiration of a person in response to a signal indicating the respiration cycle of the person.

A variety of persons such as sick patients and infants benefit from mechanically assisted respiration. In hospitals, respirators are commonly used to assist such persons to breathe. Conventional neonatal respirators deliver gases under pressure in a closed chamber (e.g. the respirator chamber) to babies. Since conventional neonatal respirators are not synchronized with patient respiration, these respirators not infrequently supply gas to infants when the infants are trying to exhale so that the infants are actually breathing against the pressured gas from the respirator. This increases the pressure in the lung and may damage lung tissues. The increase in pressure in the lung may hinder the flow of blood from the brain to the lung, thereby increasing the risk of intracranial hemorrhage.

Because of the above described disadvantages of conventional neonatal respirators, improved designs have been proposed. In one improved design, the change in gas pressure in the chamber is monitored in order to detect spontaneous respiration of the baby. A valve for ventilating the chamber to the atmosphere is then closed or opened in response to detection of inspiration and exhalation by the baby. These neonatal respirators, however, are disadvantageous since they are relatively insensitive to the spontaneous respiration of infants due to a number of factors. The respirator chamber under pressure is relatively large compared to the amount of gas inhaled or exhaled by infants which is usually in the range of five to twenty cubic centimeters. Therefore the inspiration and exhalation of infants will only cause a slight change in pressure of the chamber; such small changes may not be detected by conventional neonatal respirators.

Premature infants frequently experience periodic lapses of respiration known as apnea. Since the improved neonatal respirators described above respond to changes in pressure, such respirators simply cease to function during apnea. Because of this and other disadvantages described above, it is desirable to provide ventilation synchronizers which are more sensitive to spontaneous respiration where the amount of gas inhaled or exhaled is small and which can assist premature infants during apnea.

SUMMARY OF THE INVENTION

One aspect of the invention is based on the observation that when a person breathes, the electrical impedance between two selected points on the person's chest will change so that the spontaneous respiration of the person can be detected from such electrical impedance. Thus an inspiration control signal may be derived from such electrical impedance by triggering the supply of gas by a respirator.

The apparatus of this invention is for controlling a respirator so that gas is supplied by the respirator to a patient at desired times to aid patient breathing. The apparatus comprises means for generating an impedance signal indicating the electrical impedance between two selected points on the patient's chest. The apparatus further comprises inspiration detecting means for deriving an inspiration control signal from the impedance signal to indicate spontaneous patient inspiration and for triggering the supply of gas by the respirator upon detection of spontaneous patient inspiration.

Another aspect of the invention is based on the observation that when a person breathes, the breathing includes an inspiration cycle during which the person inhales continuously and an exhalation cycle during which the person exhales continuously, and that if a signal is generated whose level rises or falls substantially continuously during the inspiration cycle and changes in level during the exhilation cycle in the direction opposite to that during the inspiration cycle, the changes in signal level can be detected to detect the inspiration and exhalation of the person. Based on such aspect, an apparatus is designed for controlling a respirator to supply gas to a patient whose respiration includes inspiration and exhalation cycles. The apparatus comprises means for generating a signal indicative of patient respiration. The signal increases or decreases substantially continuously in amplitude during the inspiration cycle and changes in amplitude during the exhilation cycle in the direction opposite to that of the inspiration cycle. The apparatus further comprises means for detecting the change in signal level which corresponds to the inspiration cycle to generate an inspiration control signal for triggering the supply of gas by the respirator upon detection of spontaneous patient inspiration.

In the preferred embodiment, the inspiration control signal causes the respirator to supply gas to the patient for a first predetermined time period and so that no gas will be supplied for a second predetermined time period either immediately after the first time period or upon detection of spontaneous exhalation by the patient. The preferred embodiment also includes means responsive to the impedance signal for detecting apnea and means for periodically triggering the supply of gas by the respirator to the patient upon detection of apnea. If so desired, the triggering and turning off of the respirator need not be synchronized with the detection of the onset of inspiration and exhalation; instead, the triggering and turning off of the respirator may be accomplished at selected times after the initiation of inspiration and exhalation. The triggering and turning off of the respirator can also be accomplished in a manner so that the effects of a wandering baseline are minimized. Such wandering baseline may be caused by physical movements by the infant which in turn causes the electrical impedance between two points on the infant's chest to change.

DETAILED DESCRIPTION OF THE INVENTION

Figure 1:
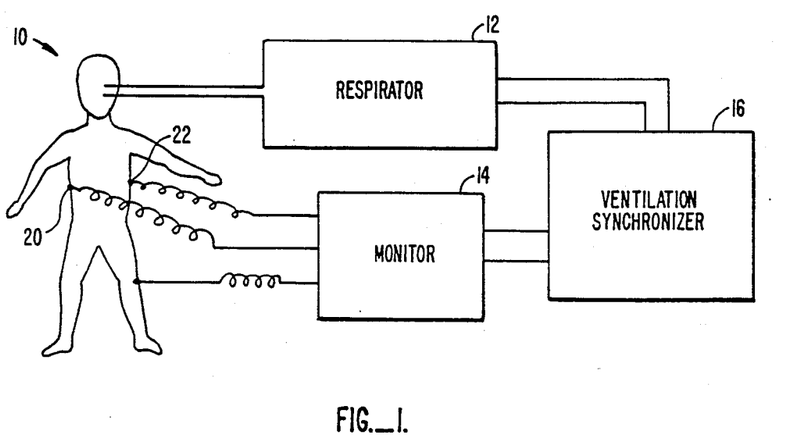
FIG. 1 is a block diagram of a respiration system connected to a patient for assisting patient respiration using a ventilation synchronizer to illustrate the invention.

FIG. 1 is a block diagram of a respiration system connected to a patient for assisting patient respiration using a ventilation synchronizer to illustrate the invention. As shown in FIG. 1, patient 10 is aided by a respirator 12 to breathe. As is frequently done in hospitals, the impedance pneumogram of patient 10 is monitored by a monitor 14. According to the teachings of this invention, a ventilation synchronizer 16 is used to take advantage of the readily accessible impedance pneumogram to synchronize the time cycles of the respirator 12 with the breathing cycles of patient 10. Impedance pneumograms are obtained by connecting wires from monitor 14 to selected points 20, 22 on the patient's chest in order to monitor the electrical impedance between points 20, 22. During the respiration cycle of the patient, the patient's chest expands during inspiration, thereby increasing the distance between points 20, 22 and increasing the electrical impedance sensed by monitor 14. When the patient exhales, the distance between points 20, 22 decreases and so does the electrical impedance sensed by monitor 14. Ventilation synchronizer 16 makes use of the information available from the electrical impedance between points 20, 22 in the impedance pneumogram to synchronize the respirator with the patient's breathing.

Figure 2:
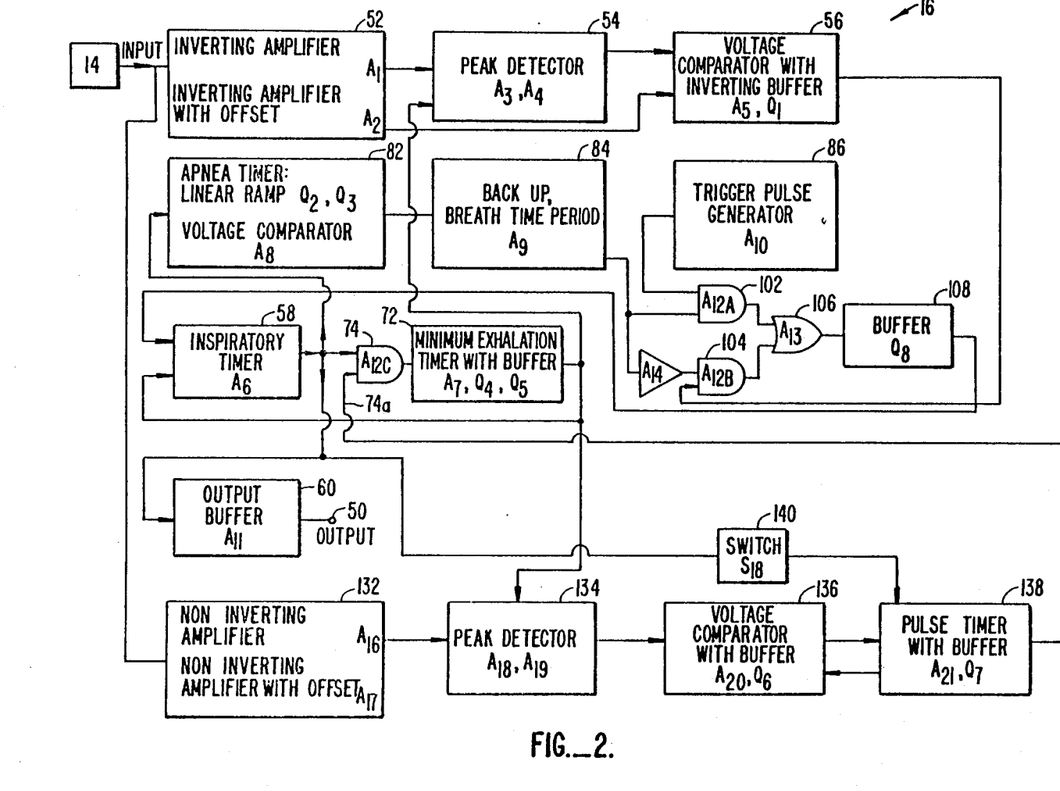
FIG. 2 is a block diagram of the ventilation synchronizer to illustrate the preferred embodiment of the invention.
Figure 3:
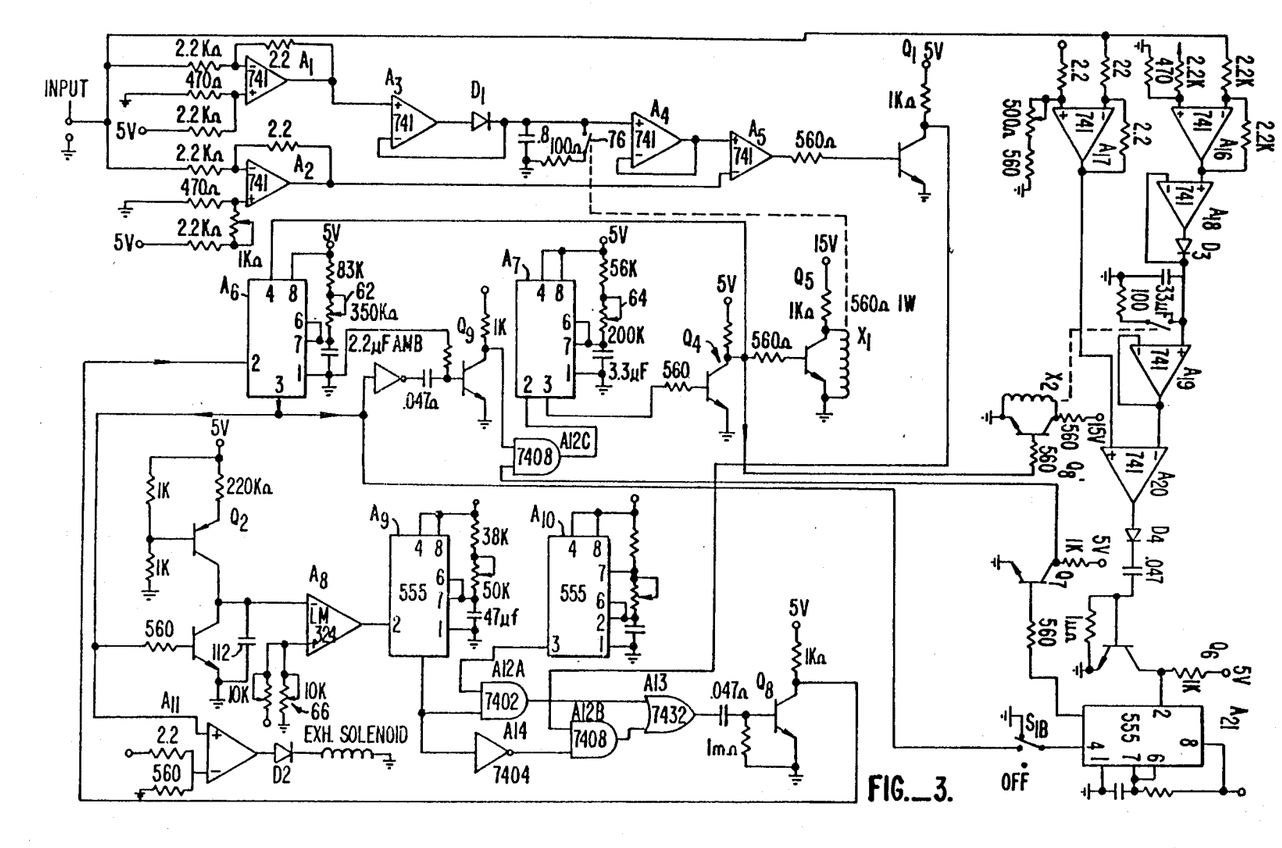
FIG. 3 is a schematic circuit diagram of the synchronizer of FIG. 2 to illustrate the preferred embodiment of the invention.

FIG. 2 is a block diagram of the ventilation synchronizer 16 of FIG. 1 to illustrate the preferred embodiment of the invention. FIG. 3 is a schematic diagram illustrating in more detail the preferred embodiment of the invention. As shown in FIG. 2, the impedance signal from monitor 14 is processed by synchronizer 16 to detect spontaneous patient inspiration in order to generate an inspiration control signal at output 50 of the synchronizer 16. The inspiration control signal is then applied to respirator 12 for controlling the supply of gas to patient 10.

The spontaneous inspiration by the patient is indicated by the rising edge of the impedance signal from monitor 14. The rising edge of the impedance signal is detected by circuit components 52-60 of FIG. 2. In the discussion that follows, reference will be made to the relevant blocks in FIG. 2 and the corresponding components in the schematic circuit diagram of synchronizer 16 in FIG. 3. In reference to FIGS. 2 and 3, the impedance signal is fed to two inverting amplifiers A1, A2. The output of inverting amplifier A1 is supplied to peak detector 54. The output of peak detector 54 and inverting amplifier A2 are applied to a voltage comparator 56. The comparator output is then applied to inspiratory timer 58 which generates the inspiration control signal. The inspiration control signal is then fed to buffer 60 whose output at 50 is used to drive a exhalation solenoid in respirator 12 (not shown in FIG. 1). The exhalation solenoid in respirator 12 controls the opening or closing of a valve of the respirator chamber to control the supply of gas to patient 10.

FIGS. 4-8 are timing diagrams to illustrate the functions of the ventilation synchronizer 16 of FIGS. 2 and 3. The detection of the rising edge of an impedance signal from monitor 14 will now be described in reference to the above-mentioned blocks in FIG. 2, the schematic illustration in FIG. 3 and timing diagrams FIGS. 4 and 5. In reference to FIGS. 2 and 3, the impedance signal is inverted by amplifiers A1, A2. For reasons discussed below, amplifier A2 also adds a DC offset.

The inverted and amplified impedance signal from amplifier A2 is then applied to peak detector 54.

Figure 4:
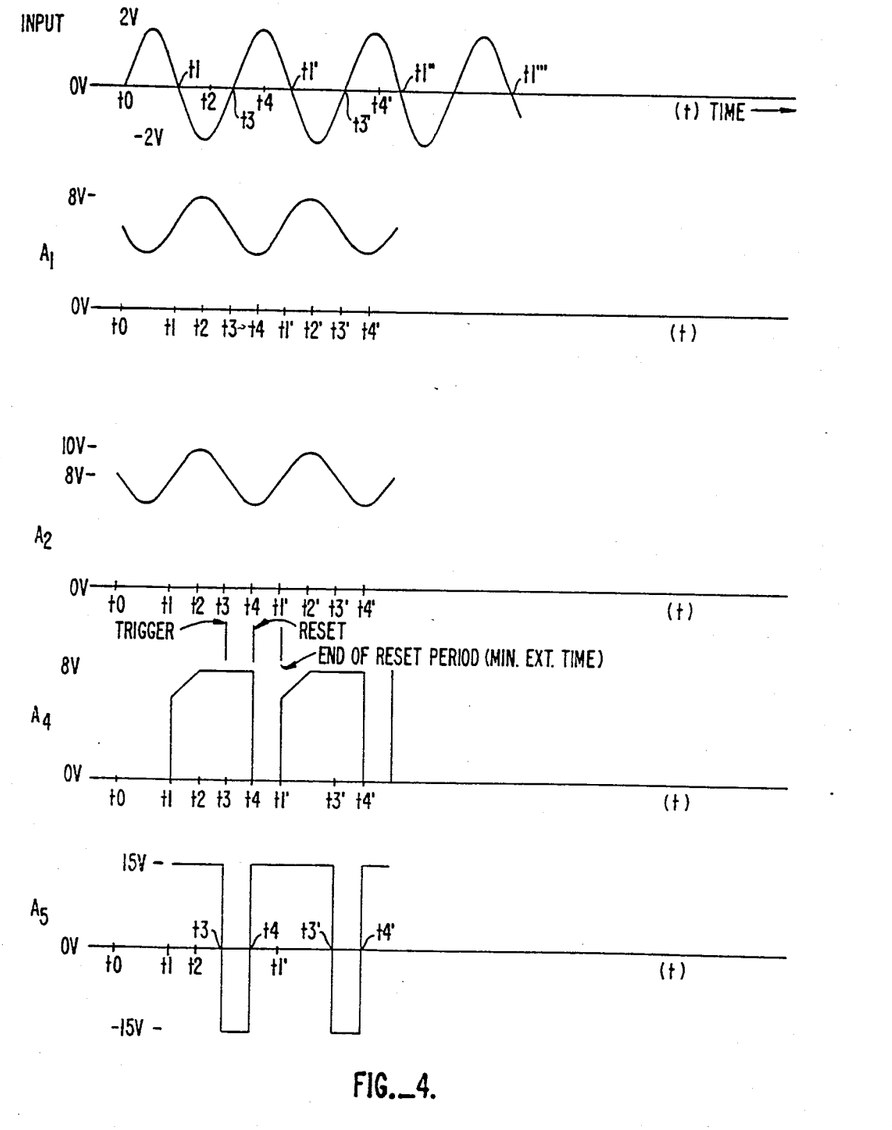
FIGS. 4–8 are timing diagrams to illustrate the functions of the ventilation synchronizer of FIGS. 2 and 3.

In reference to FIG. 4, the input signal is essentially in the shape of a sine curve. Below the input curve are shown the outputs of components A1-A5. Thus, as shown in FIG. 4, amplifier A2 adds a DC offset voltage of 2 volts to the inverted waveform of the impedance signal. At time t0, the patient is in the middle of an inspiration cycle. The inspiration cycle ends when the impedance signal reaches the peak whereupon the expiration cycle begins. The exhalation cycle ends at time t2. At time t1, peak detector 54 is switched on after a reset period described below and follows the output of amplifier A1 to 6 volts. From time t1 to t2, no peak is detected by detector 54 so that the output of the detector simply follows the output of amplifier A1. At time t2, however, a peak is detected by detector 54 so that even though the output of amplifier A1 decreases, the output of A4 remains at the peak voltage of 8 volts. The outputs of detector 54 and amplifier A2 are applied to comparator 56. At time t3, comparator 56 detects that both inputs are at 8 volts. Upon such detection, the output of A5 drops from 15 volts to −15 volts at time t3. The output of comparator 56 is clipped and inverted by transistor Q1. The output of Q1 is converted into sharp negative pulses by transistor Q8 of FIG. 3 and applied to monostable multivibrator A6 in timer 58. Timer 58 includes a monostable multivibrator A6 which is triggered by negative going pulses. Upon being triggered, timer 58 generates an output which is constant for a set time period to turn on the respirator 12 for such time period.

It will be observed that one advantage in the arrangement of amplifiers A1, A2, detector 54, comparator 56 of FIGS. 2 and 3 is that the triggering of the supply of gas from respirator 12 can be synchronized with any selected point during the spontaneous inspiration of the patient. Thus, from FIG. 4, where the offset applied by amplifier A2 is a positive DC offset, the effect is to shift the trigger point (i.e. when gas starts to flow from the respirator to the patient) to a later time after the initiation of spontaneous inspiration. As shown in FIG. 4, spontaneous inspiration is initiated at time t2, but the trigger point of the respirator is at t3, which is approximately half way in the spontaneous inspiration cycle.

In some situations, it may be desirable to shift the trigger point of the respirator to a later time after the initiation of spontaneous inspiration. For example, the patient may be breathing harder at a later point in the inspiration cycle; if that is the case, it is desirable to aid inspiration just about the time when the patient is beginning to breathe harder. Conversely, the trigger point of the respirator can be shifted close to or at the initiation of spontaneous inspiration. Thus, if no DC offset is applied by amplifier A2, the trigger point of the respirator will be at time t2, or at the onset of spontaneous inspiration. Thus, by adjusting the DC offset level in amplifier A2, the trigger point of the respirator can be synchronized with a selected point on the rising edge of the impedance signal, or in other words, at a selected point in the spontaneous inspiration cycle.

Figure 6:
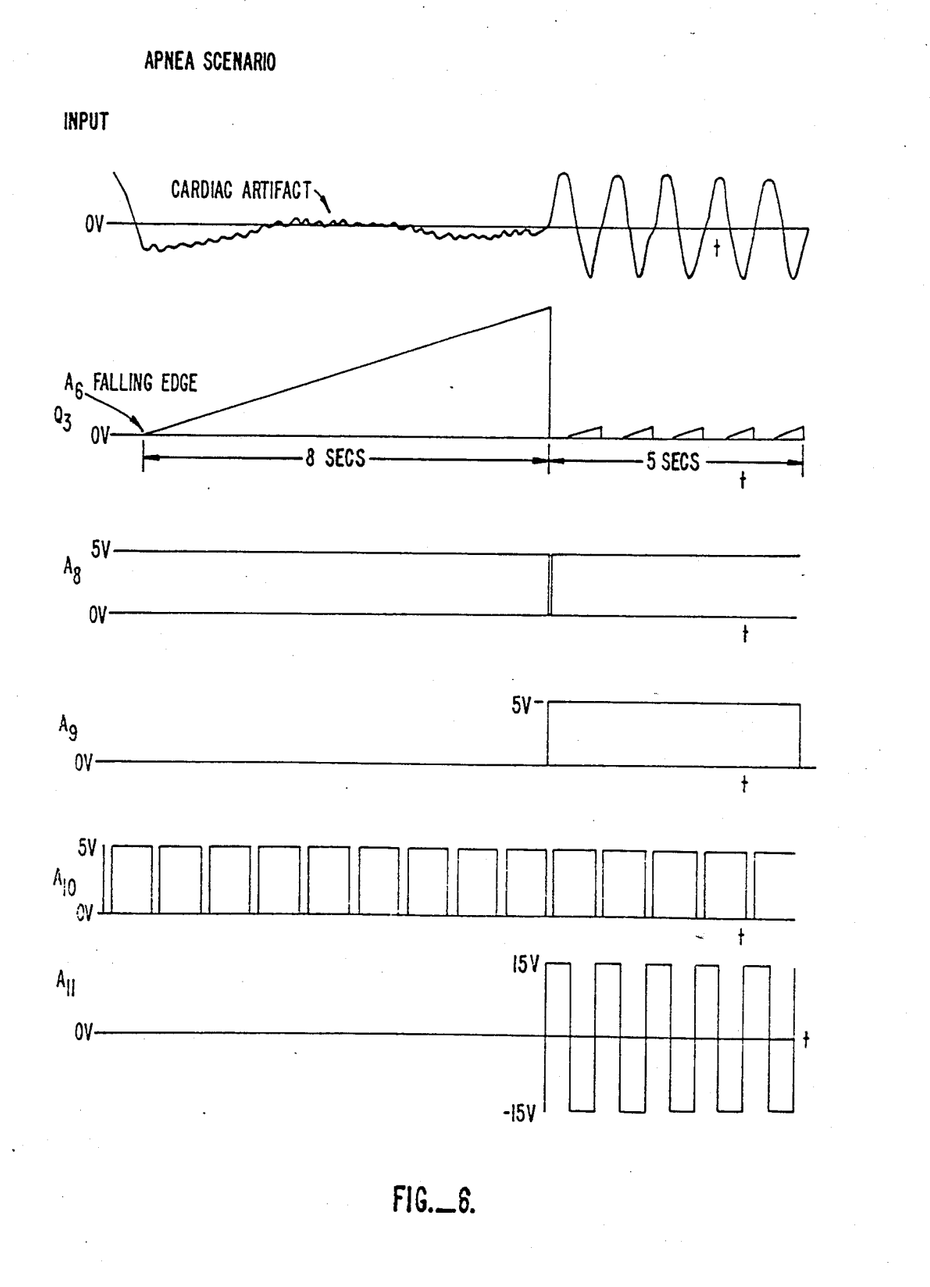

The arrangement of FIGS. 2, 3 is also advantageous since it substantially reduces the chances of triggering the supply of gas to the patient by spurious artifacts. Cardiac artifacts (i.e. heartbeat) may cause some small oscillating changes in the electrical impedance across the points 20, 22 in FIG. 1, and such oscillations appear in the input signal to synchronizer 16 as shown in the top of FIG. 6. By choosing an appropriate offset voltage at amplifier A2, the trigger point is moved away from the lowest dip point in the input impedance waveform (e.g. at time t2) so that these small oscillating changes at or near such dip points will not cause the respirator to be triggered.

Another advantage of the arrangement in FIGS. 2 and 3 is that a wandering baseline for the impedance signal and artifacts does not significantly affect the ventilation synchronizer 16. The movement of the patient, particularly infants, may cause a DC shift in the impedance signal again as shown in the top of FIG. 6, where the baseline of the impedance input signal deviates from 0 volts. Thus, if the amplitude of the impedance signal from monitor 14 is used for synchronizing the respirator, such wandering baseline caused by artifacts such as the cardiac artifact will introduce errors in the synchronization. In the arrangement in FIGS. 2 and 3, this problem is avoided by using peak detectors to minimize the effects of DC shifts on the synchronizations.

The width of the pulse at the output of timer 58 is preset in order to set the inspiration time; in other words, the inspiration time period during which the respirator supplies gas to the patient is preset in timer 58. In reference to FIG. 3, this may be set by means of moving the arrow in the 350 kilo ohms potentiometer 62 near the monostable multivibrator A6 to the appropriate point. When the timer 58 times out, a minimum exhalation timer with buffer 72 is triggered through gate 74. Timer 72 is preset to time out after a second predetermined time period. When timer 72 is counting and before it times out, timer 72 inhibits the inspiratory timer 58 to prevent respirator 12 from supplying gas to the patient during the second predetermined time period, referred to below as the minimum exhalation time period. In other words, within such minimum exhalation time period, respirator 12 is prevented from supplying gas to patient 10 irrespective of the signal conditions of the impedance signal. This feature allows the patient to exhale without having to overcome gas pressure supplied by the respirator. This feature also prevents inadvertent positive and expiratory pressure when the patient attempts to inhale without exhaling after taking in an initial breath. Taking in repeated breaths without exhaling is undesirable since pressure will build up cumulatively in the lung.

Figure 5:
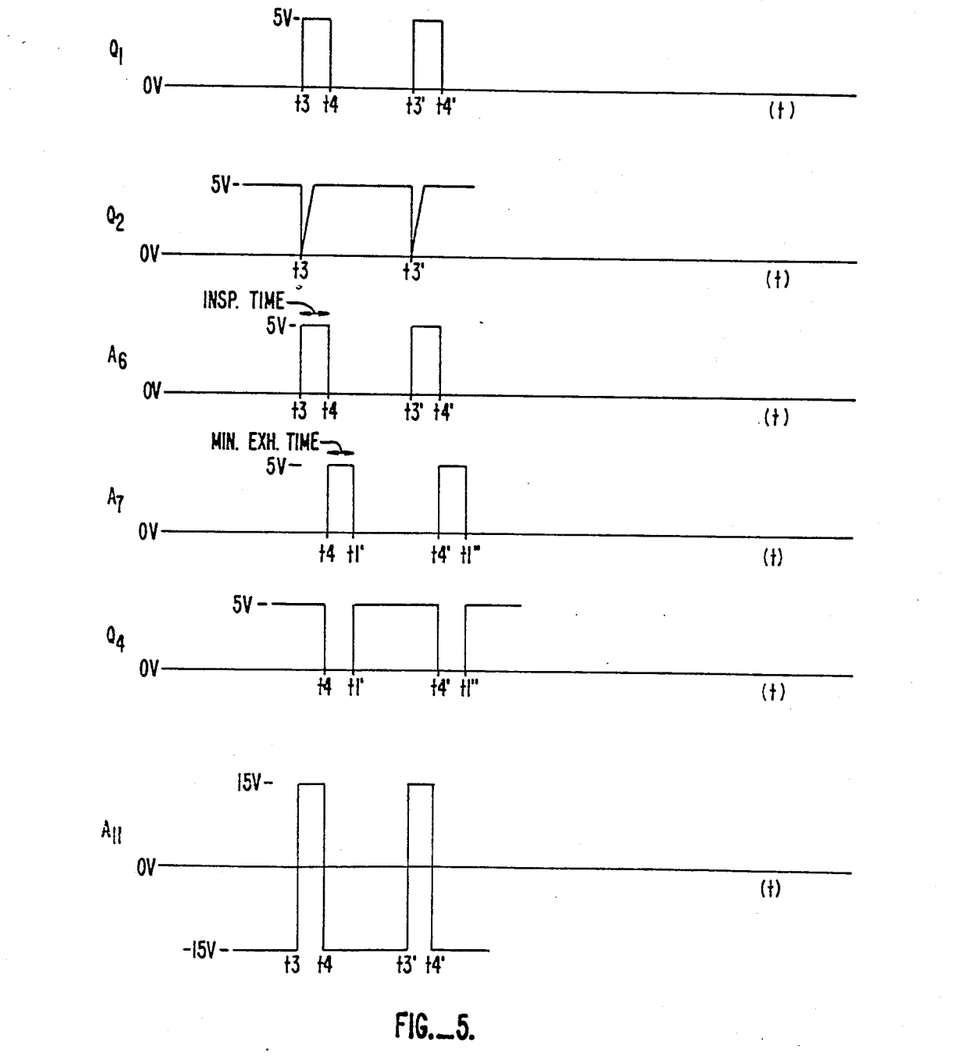

Synchronizer 16 may be operated in two different modes. In one mode, input 74a to gate 74 is always high so that the falling edge of the output of timer 58 would trigger timer 72 as shown in FIG. 5. As shown in FIG. 3, this is accomplished by an inverter, a waveshaping filter and transistor Q9, which generates a negative going pulse in response to the falling edge of the output of A6. Such negative going pulse triggers monostable multivibrator A7. The minimum exhalation time period can again be set by moving the arrow in the 200 kilo ohms potentiometer 64.

When the synchronizer 16 is operated in the other mode, the state of the input 74a to gate 74 would depend on an exhalation control signal derived from the falling edge of the impedance edge as described below. Upon the detection of the falling edge of the output of multivibrator A6 at multivibrator A7, peak detector 54 is reset by means of the output of transistor Q4. Thus, in reference to FIGS. 3 and 5, at time t4, the output of transistor Q4 goes low, which resets multivibrator A6 and peak detector 54, (and peak detector 134 as well as described below) by closing switch 76 (FIG. 3) in peak detector 54 by means of driver Q5 and relay coil X1. By closing switch 76, the output of non-inverting amplifier A4 drops to 0 volts as shown in FIG. 4. When the exhalation timer 72 times out at time t1' in reference to FIG. 5, the output of transistor Q4 rises to 5 volts. This opens the switch 76 so that the output of non-inverting amplifier A4 rises to the voltage level of the output of amplifier A1 as described above. Thus, time t1' marks the end of the reset time period. At this point, synchronizer 16 is ready to detect a selected point on the rising edge of the next spontaneous inspiration time period to repeat the above operation.

Premature infants frequently experience lapses of spontaneous respiration known as apnea. Synchronizer 16 detects apnea conditions and causes respirator 12 to supply gas to patient 10 periodically at a predetermined frequency for a set time period in order to help the patient to again initiate spontaneous respiration. Such feature of the invention is illustrated with respect to the apnea timer 82, the backup breath timer 84, trigger pulse generator 86, gates 102–106, buffer 108, the inspiration control circuitry discussed above and FIG. 6. As shown in the top of FIG. 6, the impedance signal indicates an apnea condition of the patient. Apnea timer 82 is triggered by the falling edge of the output of multivibrator A6. As shown in FIG. 6, at the falling edge of multivibrator A6, the output at the collector of Q3 rises (see FIG. 3). This charges capacitor 112. If spontaneous patient respiration continues so that there is another output pulse from multivibrator A6, this will cause transistor Q3 to conduct, thereby discharging capacitor 112. However, during apnea, multivibrator A6 will provide no output, so that the output voltage of Q3 (which also appears across capacitor 112) continues to rise as shown in FIG. 6. When the output voltage of Q3 rises to a predetermined value set with the aid of potentiometers 66 at the positive input of comparator A8, this causes a sharp negative pulse at the output of comparator A8 as shown in FIG. 6. In one implementation illustrated in FIG. 6, the values of the potentiometers are set so that the output of comparator A8 will provide its sharp negative pulse if no output is detected from multivibrator A6 for 8 seconds. Obviously other values may be chosen to for the time interval. This sharp negative pulse from comparator A8 will trigger the backup timer A9.

In the configuration of FIG. 3 and FIG. 6, timer A9 is set for about 5 seconds. Upon receiving a negative pulse from comparator A8, the output of timer A9 goes high. This output is inverted by inverter A14 and disables the AND-gate 104 (A12B), thereby causing the AND-gate output to go low at all times. The output of timer A9 causes AND-gate 102 (A12A) to pass the pulses generated by pulse generator A10. Such pulses are passed by OR-gate A13, inverted by transistor Q8 to trigger multivibrator A6 in inspiratory timer 58. In such manner, the generation of the inspiration control signal in multivibrator A6 is controlled by pulses from pulse generator A10 for the time period set by backup breath timer 84 (A9). In other words, if no spontaneous inspiration is detected for a set time period (e.g. 8 seconds), artificially generated inspiration control signals are generated with the aid of pulse generator A10 to cause inspirator 12 to supply gas to the patient periodically to help reinitiate patient spontaneous inspiration. Inverter A14, gates 102–106 (gates A12A, A12B, A13) assist in turning over control of the inspiratory timer 58 to the pulse generator A10 instead of blocks 52–56 of FIG. 2.

When a backup breath time period in timer 84 (A9) times out, the output of A9 goes low, thereby forcing the output of gate 102 (A12A) to go low, and enabling the output of comparator 56 to again be in control of timer 58, thereby causing timer 58 to be controlled by blocks 52–56 instead of the apnea circuitry 82–86 of FIG. 2.

In the mode of operation of synchronizer 16 described above, upon the expiration of the inspiration time set in timer 58, the supply of gas by respirator 12 to patient 10 is prevented for a minimum exhalation time period set in timer 72. As described above, this is accomplished by inhibiting timer 58. Such minimum exhalation time period is important since it prevents the respirator from supplying gas to the patient when the patient is exhaling and also prevents inadvertent positive and expiratory pressure. If gas is supplied while the patient is exhaling, this will increase pressure in the air sacs in the lungs of the patient. For weak adults and infants, such abnormal increase in pressure in the lungs may damage the lung tissues. The increase in lung pressure may also prevent blood flow from blood vessels in the brain towards the lung in weak patients and infants. Such increase in blood pressure in the brain may cause intracranial hemorrhage. Therefore it is crucial to prevent the respirator 12 from supplying gas to the patient while the patient is exhaling. For some patients, this is accomplished by preventing the supply of gas after the inspiratory time period determined by timer 58 for a predetermined set minimum exhalation time period which starts immediately after the inspiration time period. For other patients, it may be desirable to detect the exhalation by the patient and prevent respirator 12 from supplying gas only after the patient exhalation has been detected. In such event, it is desirable to detect patient exhalation. This is accomplished by means of blocks 132–140 in cooperation with the remaining circuitry of FIG. 2.

If the minimum exhalation time period is to begin immediately after the inspiration time period set by timer 58, switch 140 is switched to one position causing input 74a to gate 74 to be always high so that gate 74 simply passes through the output of timer 58 to timer 72 to accomplish the various functions during such mode described above. However, if the minimum exhalation time period is not to begin until exhalation is detected, switch 140 is switched to the other position so that input 74a of gate 74 is controlled by blocks 132–138. The functions of blocks 132–138 will be described in connection with their schematic implementation in FIG. 3 and the timing diagrams FIG. 7 and 8. Amplifiers A16, A17 are non-inverting amplifiers where amplifier A17 adds a DC offset. The output of amplifier A16 is applied to peak detector 134. In reference to FIG. 7, at time t11, the output of peak detector A19 simply follows the output of amplifier A16 until the output of A16 reaches its peak. Such peak marks the onset of patient exhalation. In reference to FIG. 3, the output of peak detector A19 drops to 0 volts as a result of the closing of switch 76' as controlled by the exhalation timer 72 in a manner analogous to the closing of switch 76 in peak detector 54 described above. At the end of the minimum exhalation time period at time t13, switch 76' is opened, so that the output of peak detector A19 follows the output of amplifier A16 to 6 volts. Immediately after time t13, the output of amplifier A16 decreases so that the peak detector output remains at its previously high level of 6 volts. When the output of amplifier A16 rises to above 6 volts at time t14, peak detector output again follows it to the peak and the cycle repeats itself. Comparator A20 compares the output of peak detector A19 and amplifier A17.

It will be noted that amplifier A17 adds essentially no offset so that the output of comparator A20 is a sharp positive pulse corresponding to the initiation of the exhalation time period by the patient. After clipping and inverting by multivibrator A21 and transistor Q7, the output of A20 is applied to the input of 74a in the form of negative going pulses essentially synchronous with the initiation of the exhalation time period by the patient. In such manner, the exhalation timer 72 is triggered at the point of detection of the onset of patient exhalation. Since gate 74 also responds to the output of timer 58, timer 72 will be triggered only after a high output from timer 58 has been detected, indicating that there has been spontaneous patient inspiration.

Figure 7:
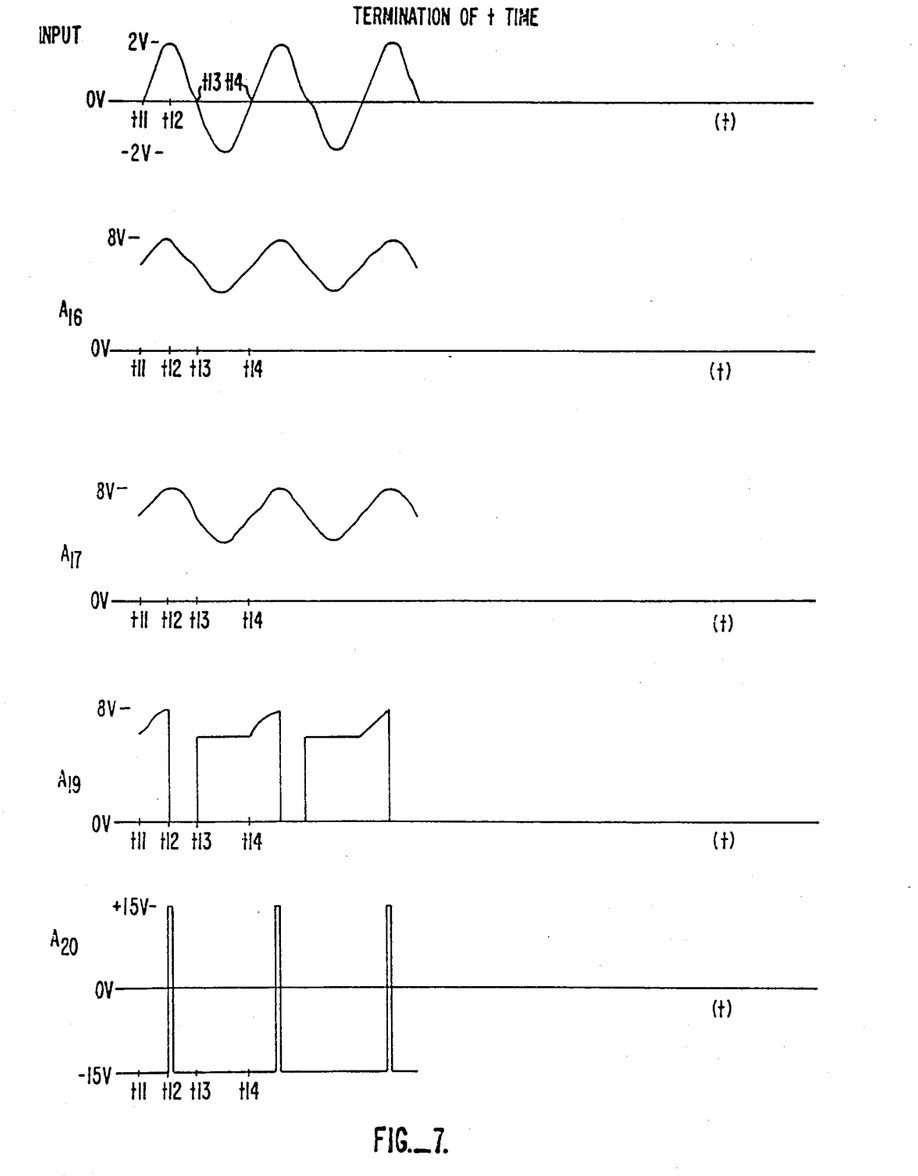
Figure 8:
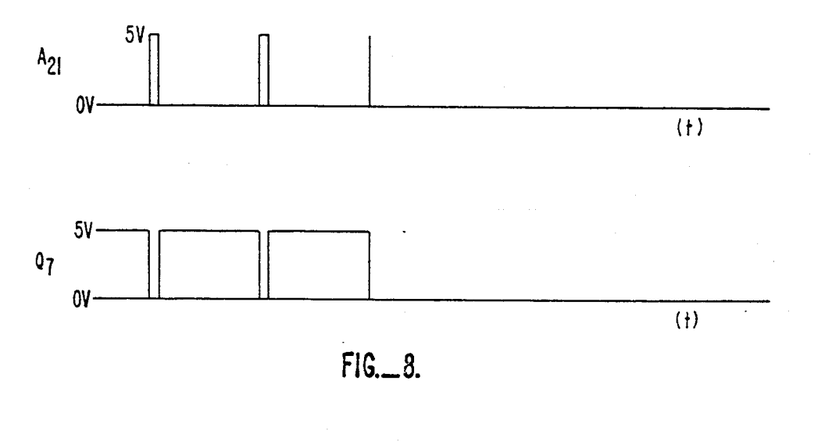

In this second mode of operation of synchronizer 16, it will be noted that, at least during the time period needed for detecting the initiation of patient exhalation, the respirator 12 will still be supplying gas to the patient, so that at least for such time period, the patient will be exhaling against gas pressure from the respirator. For this reason it is desirable to minimize the time period during which this occurs. This may be accomplished by choosing an essentially 0 DC offset in amplifier A17 as illustrated in FIGS. 7 and 8. In such manner, the triggering of the minimum exhalation time period begins almost instantaneously upon the ending of the inspiration time period of timer 58.

In the above discussion, the control of the respirator is accomplished by means of information derived from a signal indicating the changes in impedance across two selective points across the patient's chest. Other parameters may be used instead of the impedance between these two points to indicate the inspiration and exhalation by the patient. It will be understood that signals measuring other patient parameters other than the impedance between such points may also be used and are within the scope of this invention as long as the signal increases or decreases in levels substantially continuously during the inspiration cycle and changes level during the exhalation cycle in the direction opposite that during the inspiration cycle. Signals that indicate a variety of patient parameters fit the above criteria. Thus, electromyogram (electrical signals indicating the movement of the patient's diaphragm), ultra-sound signals indicating diaphragm movement in patients, pace maker signals, signals from a pneumatic transducer placed on top of the abdomen of the patient or electrical signals indicating chest muscle contractions may all be used to indicate the inspiration and exhalation cycles of the patient. When such signals are fed to ventilation synchronizer 16 of this application, synchronizer 16 will function in exactly the same manner as described above for controlling respirator 12 supplying gas to the patient. Where such signals have opposite polarity to the impedance signal illustrated in the figures of this application (i.e. where signal level decreases during the inspiration cycle and increases during the exhalation cycle), the circuitry of synchronizer 16 needs to be modified only slightly to accommodate such signals. For example, inverting amplifiers A1, A2 may be replaced by non-inverting amplifiers and non-inverting amplifiers A16, A17 replaced by inverting amplifiers. Such modification may also be made in the event that the impedance signal has a polarity opposite to that illustrated in the figures (in other words, the impedance signal decreases in amplitude during the inspiration cycle and increases in amplitude during the exhalation cycle). All such different variations and arrangements are within the scope of the invention.

The above described details of the invention pertain to the preferred embodiment. It will be obvious that other implementations may also be used that are within the scope of the invention. For example, other circuitry for detecting the rising and falling edges of the impedance signal may be used to indicate selected points in the inspiration and exhalation time period. If it is desirable to trigger the beginning of the minimum exhalation time period at a certain time after the onset of exhalation, this may be accomplished by selecting the appropriate DC offset voltage for amplifier A17 in a manner similar to that for triggering at a selected point during the inspiration time cycle. Other details of implementation and methods may also be within the scope of the appended claims.

We claim:

1. An apparatus for supplying gas under pressure to a patient at desired times to aid patient breathing, said apparatus comprising: a respirator
    means for generating an impedance signal having at least one rising edge indicative of the electrical impedance between two selected locations on the patient's chest, said locations being spaced apart from each other; and
    inspiration detecting means for deriving an inspiration control signal from the impedance signal to indicate spontaneous patient inspiration and for triggering the respirator to supply gas under pressure to at-least one of the patient's lungs by the respirator upon detection of spontaneous patient inspiration, wherein said inspiration detecting means comprises:
    means for inverting the impedance signal;
    means for adding to the inverted impedance signal a selected DC offset to obtain a sum signal;
    a peak detector including means for generating an output signal for detecting the peaks of the inverted impedance signal; and
    means for comparing the peak detector output signal with the sum signal for generating the inspiration control signal, wherein the DC offset determines the point on the rising edge of the impedance signal at which the triggering of the respirator is synchronized.

2. An apparatus for supplying gas under pressure to a patient at desired times to aid patient breathing, said apparatus comprising: a respirator
    means for generating an impedance signal having at least one rising edge indicative of the electrical impedance between two selected locations on the patient's chest, said locations being spaced apart from each other; and
    inspiration detecting means for deriving an inspiration control signal from the impedance signal to indicate spontaneous patient inspiration and for triggering the respirator to supply gas under pressure to at least one of the patient's lungs by the respirator upon detection of spontaneous patient inspiration, wherein said inspiration detecting means comprises:
    means for adding to the impedance signal a selected DC offset to obtain a sum signal;
    a peak detector including means for generating an output signal for detecting the peaks of the impedance signal; and
    comparing means including means for generating an output signal for comparing the peak detector output with the sum signal for detecting the rising edge and for generating the inspiration control signal.

3. The apparatus of claim 2, wherein said inspiration detecting means further comprises an inspiration timer responsive to the comparing means output signal for generating the inspiration control signal to control the respirator for supplying gas for a first time period.

4. The apparatus of claim 3, wherein said inspiration detecting means further comprises an exhalation timer responsive to the inspiration control signal for preventing the respirator from supplying gas to the patient for a second time period to permit exhalation.

5. An apparatus for supplying gas under pressure by the respirator to a patient at desired times to aid patient breathing, said apparatus comprising: a respirator
    means for generating an impedance signal having at least one falling edge indicative of the electrical impedance between two selected locations on the patient's chest, said locations being spaced apart form each other; and
    inspiration detecting means for deriving an inspiration control signal from the impedance signal to indicate spontaneous patient inspiration and for triggering the respirator to supply gas under pressure to at least one of the patient's lungs by the respirator upon detection of spontaneous patient inspiration, said apparatus further comprising exhalation detecting means for generating an exhalation control signal from the impedance signal to indicate patient exhalation, wherein the inspiration and exhalation control signals control the respirator so that no gas will be supplied by the respirator for a second predetermined time period upon detection of exhalation by the detecting means, wherein said exhalation detecting means further comprises an exhalation timer, said apparatus further comprising a gating means responsive to the inspiration and exhalation timer to prevent the respirator from supplying gas to the patient for the second time period only when the inspiration control signal indicates the presence of spontaneous inspiration and the exhalation control signal indicates the presence of spontaneous exhalation, wherein said exhalation detecting means comprises:
    means for adding to the impedance signal a selected DC offset to obtain a sum signal;
    a peak detector including means for generating an output signal for detecting the peaks of the impedance signal; and
    means for comparing the peak detector output signal with the sum signal for generating the exhalation control signal, wherein the DC offset determines the point on the falling edge of the impedance signal at which gas supplied by the respirator is shut off.

6. An apparatus for supplying gas under pressure to a patient at desired times to aid patient breathing, said apparatus comprising: a respirator
    means for generating an impedance signal having at least one rising edge indicative of the elctrical impedance between two selected locations on the patient's chest, said locations being spaced apart from each other; and inspiration detecting means for deriving an inspiration control signal from the impedance signal to indicate spontaneous patient inspiration and for triggering the respirator to supply gas under pressure to at least one of the patient's lungs by the respirator upon detection of spontaneous patient inspiration, wherein said inspiration detecting means comprises:

means for adding to the impedance signal or a signal derived from the impedance signal a selected DC offset to obtain a sum signal;

a peak detector including means for generating an output signal for detecting the peaks of the impedance signal or the peaks of the derived signal; and means for comparing the peak detector output signal with the sum signal for generating the inspiration control signal, wherein the DC offset determines the point on the rising edge of the impedance signal at which the triggering of the respirator is synchronized.

* * * * *